(12) United States Patent
Green et al.

(10) Patent No.: US 6,409,730 B1
(45) Date of Patent: Jun. 25, 2002

(54) HUMERAL SPIRAL BLADE

(75) Inventors: James M. Green, Portland, OR (US); Stanley J. Kmiec, Jr., Coopersburg, PA (US)

(73) Assignee: Synthes (USA), Paoli, PA (US)

( * ) Notice: Subject to any disclaimer, the term of this patent is extended or adjusted under 35 U.S.C. 154(b) by 150 days.

(21) Appl. No.: 09/584,381

(22) Filed: May 31, 2000

(51) Int. Cl.⁷ .................................................. A61B 17/84
(52) U.S. Cl. ............................. 606/72; 606/67; 606/65
(58) Field of Search .............................. 606/60, 65, 66, 606/67, 68, 72, 75, 62, 63, 64

(56) References Cited

U.S. PATENT DOCUMENTS

| | | |
|---|---|---|
| 1,951,278 A | 3/1934 | Ericsson |
| 2,187,852 A | 1/1940 | Friddle |
| 2,235,419 A | 3/1941 | Callahan et al. |
| 2,486,136 A | 10/1949 | Ericsson |
| 2,496,126 A | 1/1950 | Haboush |
| 2,557,669 A | 6/1951 | Lloyd |
| 2,612,159 A | 9/1952 | Collison |
| 2,621,653 A | 12/1952 | Briggs |
| 2,628,614 A | 1/1953 | Briggs |
| 2,627,855 A | 2/1953 | Price |
| 2,702,543 A | 2/1955 | Pugh |
| 2,834,342 A | 5/1958 | Yost |
| 3,002,514 A | 10/1961 | Deyerle |
| 3,025,853 A | 3/1962 | Mason |
| 3,029,811 A | 4/1962 | Yost |
| 3,561,437 A | 2/1971 | Orlich |
| 4,009,712 A | 3/1977 | Burstein et al. |
| 4,103,683 A | 8/1978 | Neufeld |
| 4,475,545 A | 10/1984 | Ender |
| 4,622,959 A | 11/1986 | Marcus |
| 4,697,585 A | 10/1987 | Williams |
| 4,770,376 A | 9/1988 | Lindblom ........................ 248/1 |
| 4,875,475 A | 10/1989 | Comte et al. |
| 4,911,153 A | 3/1990 | Border ........................... 606/98 |
| 4,976,258 A | 12/1990 | Richter et al. ................. 606/64 |
| 4,978,349 A | 12/1990 | Frigg ............................ 606/67 |
| 5,032,125 A | 7/1991 | Durham et al. ............... 606/62 |
| 5,041,115 A | 8/1991 | Frigg et al. ................... 606/62 |
| 5,116,336 A | 5/1992 | Frigg ............................ 606/65 |
| 5,129,901 A | 7/1992 | Decoste ........................ 606/65 |
| 5,176,681 A | 1/1993 | Lawes et al. .................. 606/64 |
| 5,201,735 A | 4/1993 | Chapman et al. ............. 606/67 |
| 5,248,313 A | 9/1993 | Greene et al. ................. 606/62 |
| 5,300,074 A | 4/1994 | Frigg ............................ 128/67 |
| 5,454,813 A | 10/1995 | Lawes ........................... 606/62 |
| 5,472,444 A | 12/1995 | Huebner et al. ............... 606/64 |
| 5,562,667 A | 10/1996 | Shuler et al. .................. 606/64 |
| 5,571,139 A | 11/1996 | Jenkins, Jr. .................. 606/232 |
| 5,573,536 A | 11/1996 | Grosse et al. ................. 606/60 |
| 5,591,168 A | 1/1997 | Judet et al. ................... 606/65 |
| 5,697,930 A | 12/1997 | Itoman et al. ................ 606/62 |
| 5,713,902 A | 2/1998 | Friedl ........................... 606/64 |
| 5,741,256 A | 4/1998 | Bresina ........................ 606/62 |
| 5,766,174 A | 6/1998 | Perry ............................ 606/62 |
| 5,908,422 A | 6/1999 | Bresina ........................ 606/67 |
| 5,928,235 A | 7/1999 | Friedl ........................... 606/64 |

FOREIGN PATENT DOCUMENTS

| | | |
|---|---|---|
| DE | 867274 | 1/1949 |
| EP | 355411 A1 | 2/1990 |
| EP | 0411273 A1 | 5/1990 |
| EP | 486483 A1 | 5/1992 |
| EP | 586824 A1 | 7/1993 |
| WO | WO 98/53746 | 1/1998 |

*Primary Examiner*—David O. Reip
(74) *Attorney, Agent, or Firm*—Pennie & Edmonds LLP

(57) ABSTRACT

An osteosynthetic implant for use in treating fractures to the head and neck of the humerus. The implant includes a body, a helically twisted blade having an oblate cross section, and a circumferential collar having a plurality of attachment points for sutures.

20 Claims, 5 Drawing Sheets

HUMERAL SPIRAL BLADE

TECHNICAL FIELD

The invention relates to an implant for internal fixation of bone and in particular to an implant for internal fixation of diaphyseal and multi-part fractures of the humerus to promote osteosynthesis. The invention can be used, for example, in conjunction with an intramedullary device containing a proximal slot for the humeral spiral blade to be positioned and provisionally locked.

BACKGROUND OF THE INVENTION

Overall between 160,000 and 180,000 individuals suffer fractures of the humerus each year. Approximately seventy five percent of fractures occur in the proximal region of the humerus near the head or cortex, ten percent occur in the mid-shaft region, and fifteen percent occur in the distal region of the humerus.

Diaphyseal humeral fractures involve the humeral shaft. Proximal humeral fractures involve fractures of the head or cortex and often result from a fall that places an axial load on the humerus. In a two-part fracture, the head or a single portion of the head is broken from the humeral shaft. Multi-part fractures involve fracture of the humeral head into two or three fragments that separate from the shaft.

Conventional treatment of diaphyseal and multi-part humeral fractures often involves wiring, suturing, or externally fixing the fragments to one another and/or the humeral shaft. Other known approaches involve inserting one or more screws into the head or shaft of the humerus and fixing the nails or screws to a nail inserted into the medullary canal of the humerus, such as those described in U.S. Pat. Nos. 4,503,847, 5,472,444, 5,697,930, and 5,766,174.

Frequent postoperative complications arise when two or more of the bone fragments are forced together as when the patient applies pressure to the healing bone. For example, a sharp implanted nail or screw may cut out and through the humeral head or neck; or a nail, screw, or intramedullary nail may bend or break under a load. Cut out is particularly problematic in individuals with poor bony stock, such as cancerous or osteoporotic bone. A need exists, therefore, to provide improved osteosynthetic implants for treatment of multi-part and diaphyseal fractures of the humerus.

Femoral fractures have been treated using single, helical blades, such as disclosed in U.S. Pat. Nos. 4,103,683, 4,978,349, and 5,300,074. These blades are twisted about ninety degrees along their length and have a generally flat rectangular profile with a substantially uniform width and narrow thickness. When implanted in conjunction with an intramedullary nail, these blades are oriented to reduce pressure on cancellous tissue within the femoral head and to provide a high resistance to bending in response to loads along the longitudinal axis of the intramedullary nail.

Because of the aforementioned narrow thickness, however, the prior art single helical femoral blades are fairly compliant in the transverse direction, i.e., in the anterior and posterior directions of the patient. Moreover, the overall flat profile of the blades provides little resistance to cutting through the cancellous bone like a knife in directions aligned with the width of the blade at any station along its length. A need exists, therefore, to provide improved osteosynthetic implants for treatment of multi-part and diaphyseal fractures of the humerus which do not have a tendency to cause such cutting and provides greater resistance to bending in the transverse direction.

Repairing a fractured humerus frequently involves repair of damaged soft tissue surrounding the humerus. Traditional suture anchors suffer from pullout in weakened bone and also require that additional holes be drilled in an already weakened humerus. U.S. Pat. No. 5,766,174 discloses an intramedullary nail having suture holes and a nail cap with suture holes. Suture holes on an intramedullary nail are often not accessible once the nail has been implanted in a fractured humerus. Thus, in repair of a fractured humerus, a need also exists to provide robust, accessible sites for suture attachment that do not require additional drilling of the fractured humerus.

SUMMARY OF THE INVENTION

The present invention relates to an implant for a bone. The implant has a body member having a lateral portion, a medial portion, and a helically twisted blade extending along the body and having a longitudinal axis. In a preferred embodiment, the lateral portion of the helically twisted blade is twisted about one fourth turn with respect to the medial portion.

The lateral portion of the body has a circumferential collar extending in a plane perpendicular to the longitudinal axis. The circumferential collar has an attachment element for attaching a tissue fastener for repairing tissue surrounding the bone. In one embodiment, the attachment element comprises a hole for securing the tissue fastener. In another embodiment, the attachment element comprises a threaded hole.

In another embodiment, the body member has a central portion between the lateral and medial portions. The central portion has a cross section and a maximum thickness adjacent the longitudinal axis which gradually tapers to a minimum thickness apart from the longitudinal axis.

In a preferred embodiment, a cannulation extends through the body member along the longitudinal axis from the medial portion to the lateral portion. In another embodiment, the circumferential collar includes a central hole configured with threads to releasably engage a tool for positioning the invention in the bone.

In another embodiment, the medial portion has a medially extending medial end portion having surfaces configured for cutting through the bone. In a preferred embodiment, the medial end portion includes first and second cutting regions and a transverse axis. The first and second cutting regions are asymmetrically disposed about the transverse axis. In a preferred embodiment, the first and second cutting regions further include cutting edges, which form an angle of about thirty degrees to the transverse axis. The first and second cutting regions may include an angled cutting surface. In a preferred embodiment, the angled cutting surfaces form an angle of from about five to sixty degrees with respect to the longitudinal axis.

The present invention also relates to an osteosynthetic apparatus for fixing a broken humerus. The apparatus includes the implant of the present invention and a securing member comprising an elongated nail having a proximal securing portion configured to occupy a proximal portion of the humeral shaft and a distal portion configured to occupy a distal portion of the humeral shaft. In a preferred embodiment, the proximal securing portion has at least one longitudinal bore configured to accommodate the implant. When the implant is accommodated by the longitudinal bore, a medial portion of the implant is preferably within the head of the humerus and the implant may be positioned and provisionally locked.

The present invention further relates to a method for fixing a broken humerus. The method includes implanting the implant of the present invention in the humerus with the medial portion of the twisted blade inside the head of the humerus. In a preferred embodiment, the circumferential collar of the implant include a plurality of holes.

BRIEF DESCRIPTION OF THE DRAWINGS

Preferred embodiments of the invention will now be described in connection with the attached drawing figures, wherein.

DETAILED DESCRIPTION OF THE INVENTION

Figure 1:
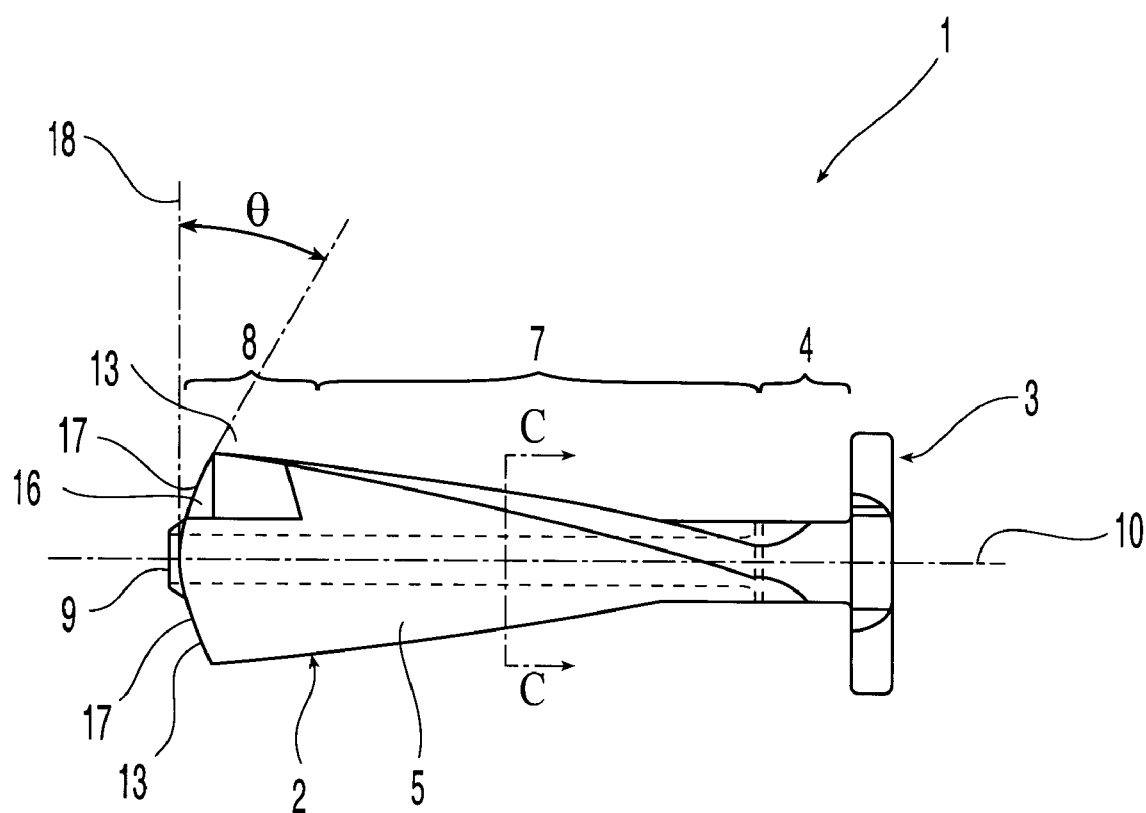
FIG. 1 is a top view of an implant according to the present invention.

In this description, the terms medial and lateral are defined in relation to the central axis of a patient. Thus, a medial portion of an implanted element according to the invention is located closer to the central axis of a patient. Similarly, the terms proximal and distal are defined in relation to the relative distance from the head of a patient. Thus, a proximal portion of an implanted element is located closer to the head of the patient than a distal portion of the element.

Referring to FIGS. 1–6, a spiral humeral blade 1 has a helically twisted blade 2 and a circumferential collar 3 adjacent and lateral to a neck portion 4 of blade 2. Blade 2 is formed by bearing surfaces 5 and side surfaces 6. Proceeding medially from neck portion 4, blade 2 also includes a central portion 7 and a medial portion 8. A cannulation 9 extends through blade 2 along a longitudinal axis 10 of spiral blade 1.

Figure 2:
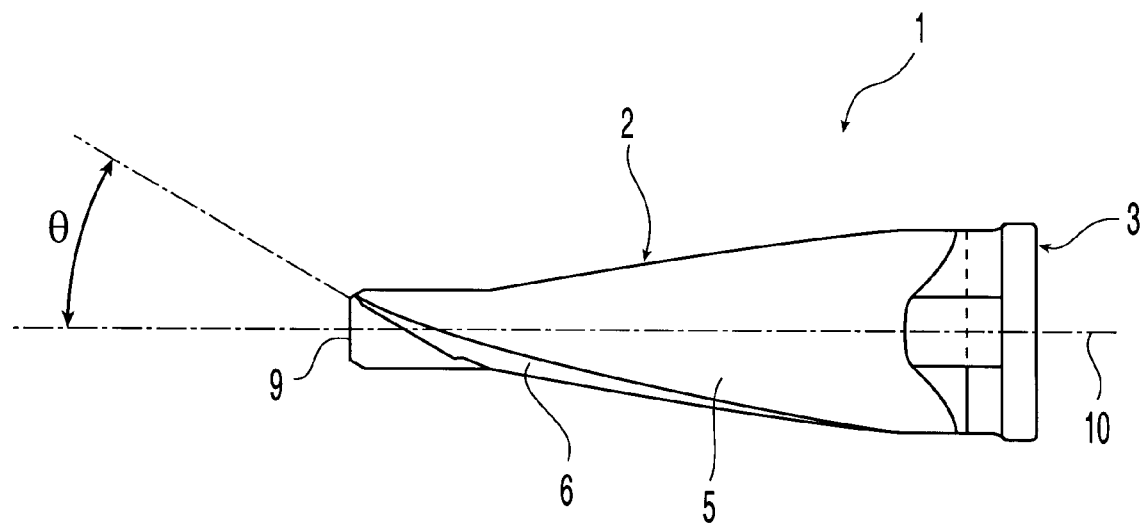
FIG. 2 is a side view of the implant shown in FIG. 1.

FIGS. 1 and 2 show that central portion 7 and medial portion 8 of blade 2 wind around longitudinal axis 10 of spiral blade 1 in a preferably contiguous manner. Blade 2 covers an angle of rotation that is at least about thirty degrees, preferably from about forty five degrees to one hundred twenty degrees, and most preferably about ninety degrees. Neck portion 4 may extend substantially straight along longitudinal axis 10 of spiral blade 1.

Figure 3:
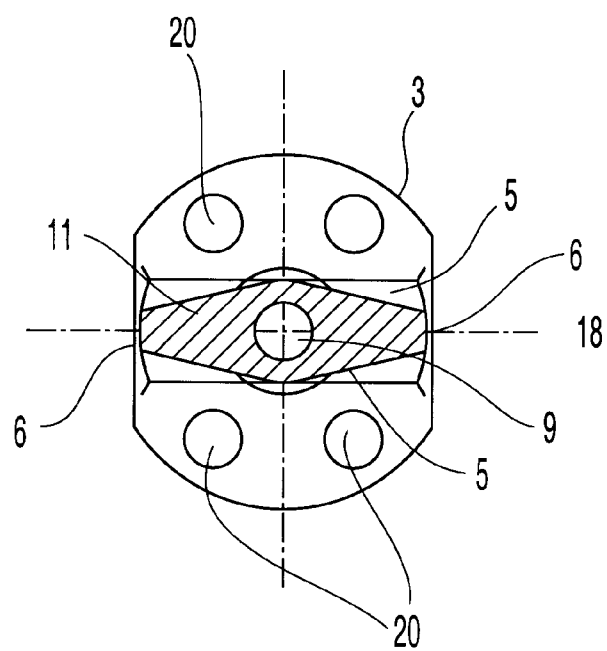
FIG. 3 shows a sectional view of an implant taken along line C—C in FIG. 1.

FIG. 3 shows a representative cross-section 11 of central portion 7 taken along section C—C in FIG. 1. Cross-section 11 is formed by opposing bearing surfaces 5 and opposing side surfaces 6. A distance separating opposing bearing surfaces 5 tapers from a maximum adjacent longitudinal axis 10 to a minimum abutting side surfaces 6. In the embodiment shown, blade 2 has a substantially uniform width at any station along longitudinal axis 10 so that sides 6 are uniformly separated along blade 2. Blade 2 may also be tapered so that a distance separating side surfaces 6 increases or decreases proceeding along blade 2 in the medial direction.

Figure 4:
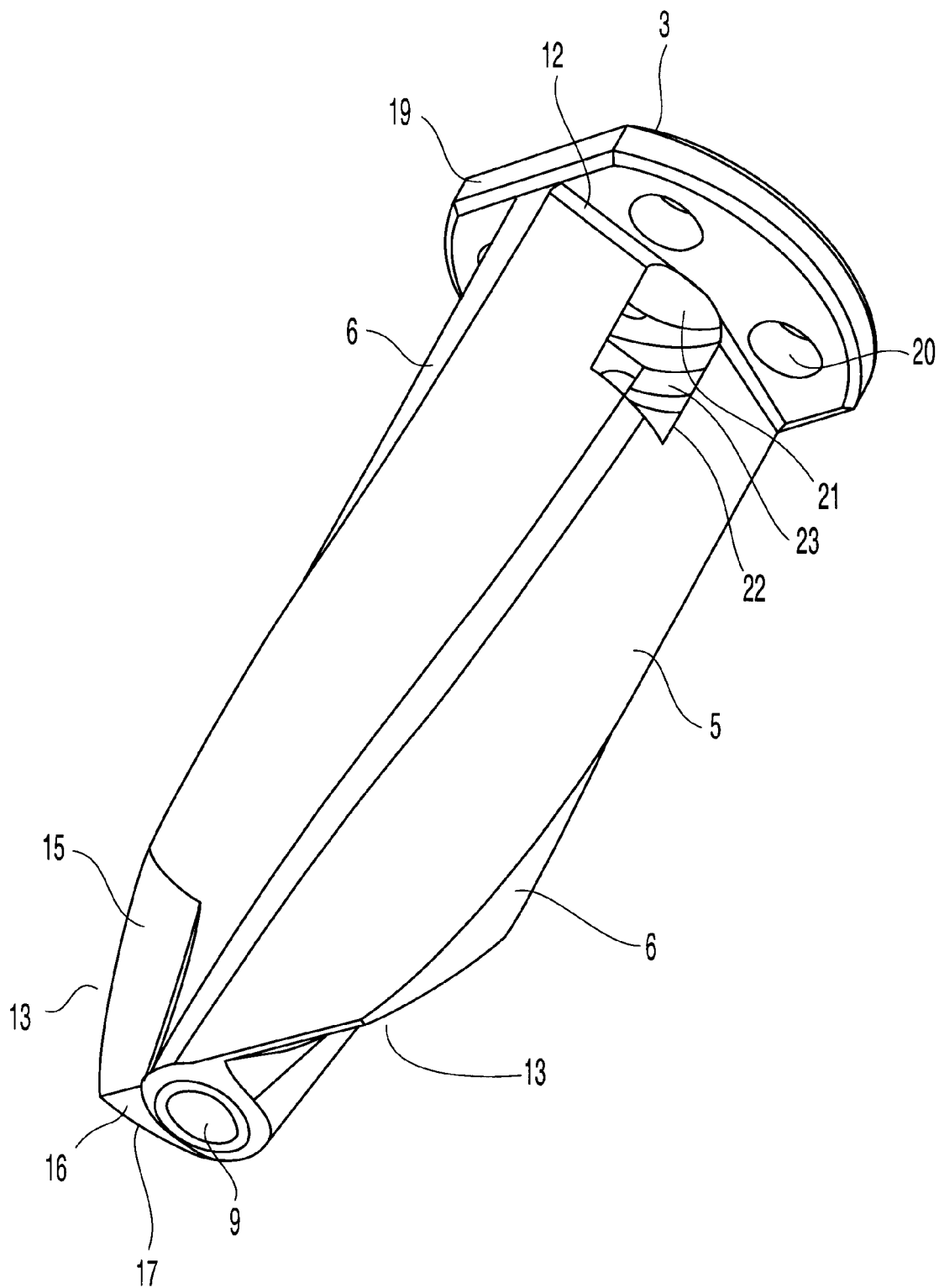
FIG. 4 is a perspective view of the implant.

As best seen in FIG. 4, neck portion 4 joins circumferential collar 3 by a smooth transition region 12. Smooth transition region 12 reduces stress risers that would otherwise result by a sharp change in geometry.

Figure 6:
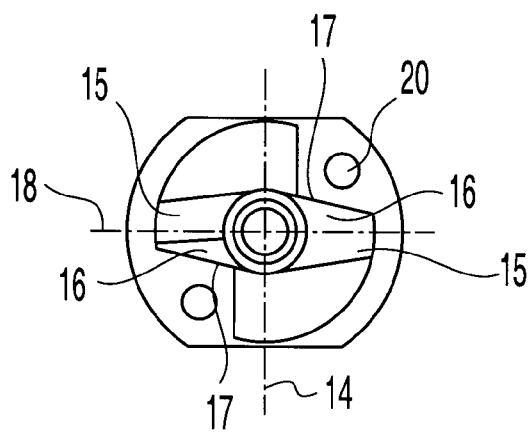
FIG. 6 shows a medial view of the implant.

In FIGS. 1 and 4 an exemplary embodiment of spiral blade 1 is shown in which medial portion 8 is configured with cutting regions 13 to facilitate implantation of spiral blade 1 into a bone. As seen in FIG. 6, cutting regions 13 are asymmetrically disposed about a first transverse axis 14 of spiral blade 1. Cutting region 13 has a first cutting surface 15 gradually tapering to meet a second cutting surface 16. Second cutting surface 16 tapers more steeply to form a medial cutting edge 17. In the embodiment shown, first cutting surface 15 is substantially planar, although first cutting surface 15 may also be arcuate. As shown in FIG. 2, a line substantially parallel to first cutting surface 15 forms an angle $\theta$ with respect to longitudinal axis 10 of spiral blade 1. Angle $\theta$ is from about five degrees to sixty degrees, preferably from about fifteen degrees to sixty degrees, and most preferably about thirty degrees. As shown in FIG. 1, medial cutting edge 17 forms an angle $\phi$ with a second transverse axis 18 of spiral blade 1. Angle $\phi$ is from about five degrees to sixty degrees, preferably from about fifteen degrees to sixty degrees, and most preferably about thirty degrees.

Figure 5:
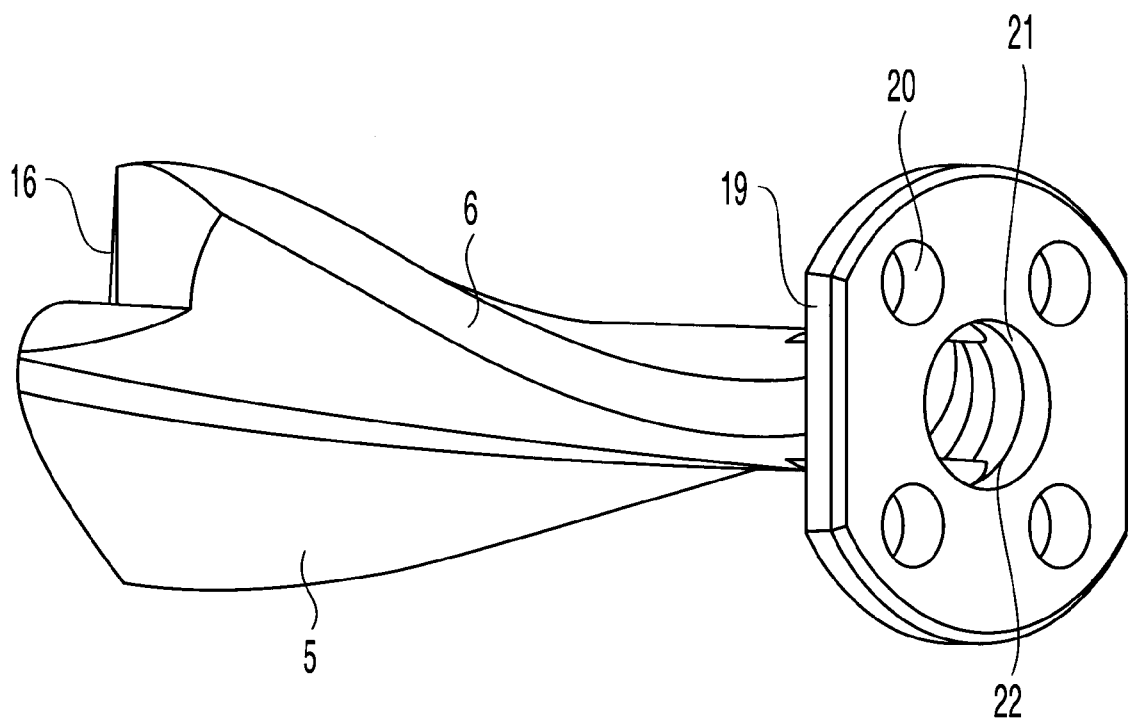
FIG. 5 shows another perspective view of the implant.

As seen best in FIGS. 4 and 5, circumferential collar 3 has a maximum diameter about as great as the width of neck portion 4 of blade 2 and is provided with flat portions 19, which allow spiral blade 1 to be positioned or moved with an auxiliary tool.

In an exemplary embodiment, circumferential collar 3 includes attachment points 20 to facilitate attachment of sutures. In a preferred embodiment, attachment points 20 comprise through-holes to which sutures may be attached. Alternatively, attachment points 20 may be configured to receive one or more auxiliary suture anchors for the fixation of sutures or other means adapted to reconstruct soft tissue, as is known in the art. In a non-limiting example, circumferential collar 3 may be configured with threaded holes to receive a threaded suture anchor.

Cannulation 9 is configured to receive a guide wire to aid in the alignment of spiral blade 1 during implantation, as is known in the art. As seen best in FIGS. 4 and 5, a central hole 21 extends through circumferential collar 3 and into neck portion 4 of blade 2. Central hole 21 has a diameter greater than the maximum separation distance of bearing surfaces 5 so that central hole 21 breaks through a portion of bearing surfaces 5 of neck portion 4 forming an aperture 22. Central hole 21 is configured with threads 23 to allow releasable attachment of a device to facilitate implantation or removal of spiral blade 1. After implantation, central hole 21 is fitted with a threaded end cap to prevent tissue ingrowth from obscuring central hole 22. The threaded end cap may also be configured with attachment points similar to attachment points 20 on circumferential collar 3.

Figure 7:
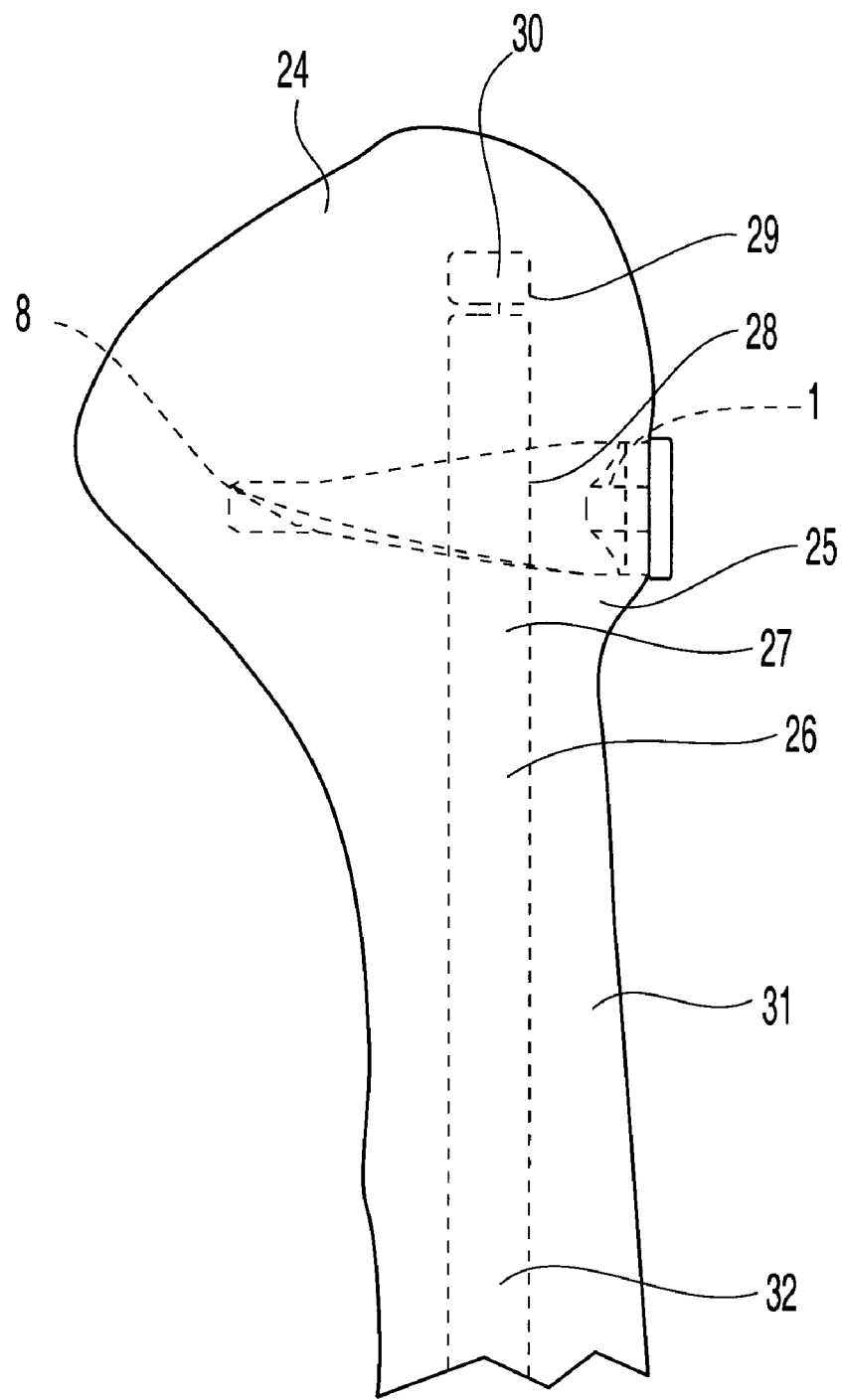
FIG. 7 shows a cross-sectional side-view of the implant implanted in a humerus in conjunction with an intramedullary nail.

In use, spiral blade 1 is implanted inside head 24 and neck 25 of the humerus, as shown in FIG. 7. Implantation procedures for fixation nails are well known in the art and can be applied with the present invention. FIG. 7 shows an embodiment utilizing an intramedullary nail 26 implanted in a humeral shaft 31. A distal portion 32 of nail 26 is configured to occupy a distal portion of humeral shaft 31 and a proximal nail portion 27 is configured to occupy a proximal portion of the humeral shaft. During implantation, intramedullary nail 26 is first inserted into the humerus.

Spiral blade 1 is then implanted through the side of humeral shaft 31 through a hole drilled merely up to the side surface of the intramedullary nail. Proximal nail portion 27 of intramedullary nail 26 includes an oblong bore 28 substantially aligned with a longitudinal axis of proximal nail portion 27. Oblong bore 28 slidably accommodates blade 2 allowing spiral blade 1 to rotate about longitudinal axis 10 as spiral blade 1 is hammered into the bone. Once implanted, longitudinal axis 10 defines an angle with the length of the intramedullary nail of generally being between ninety degrees and one hundred fifty degrees. The angle is adjusted to accommodate the anatomy of the patient.

A proximal bore 29 of intramedullary nail 26 can accommodate, for example by threaded engagement, a locking end cap 30. Engaging locking end cap 30 with proximal bore 29 applies an axial force against medial portion 7 of spiral blade 1 disposed in oblong bore 29. By means of locking end cap 30, axial movement of spiral blade 1 within oblong bore 29 can be either limited or completely prevented.

Neck portion 4 of an implanted spiral blade 1 is oriented to present a relatively small surface area normal to loads imposed substantially along humeral shaft 31, thereby, increasing the bending stiffness of blade 2 in response to such loads and also transferring a portion of the load to intramedullary nail 26. Medial portion 8 of an implanted spiral blade 1 is oriented to present a relatively large surface area normal to loads imposed substantially along humeral shaft 31. This reduces pressure on cancellous tissue within humeral head 24 and resists the tendency of blade 2 to cut through further through the bone cortex.

As shown in FIG. 7, circumferential collar 3 of an implanted spiral blade 1 remains exposed adjacent to humeral head 24, which allows access to attachment points 20. Configuring circumferential collar 3 of spiral blade 1 with attachment points 20 has several advantages over conventional suture anchors. First, when implanted, circumferential collar 3 is disposed laterally with respect to head 24 of a humerus, which provides a convenient and accessible location for suture attachment. Circumferential collar 3 is large enough to accommodate a plurality of attachment points, which reduces the need to place additional anchors in the bone. Additionally, because spiral blade 1 is firmly implanted in head 24 of a humerus in conjunction with intramedullary nail 26, circumferential collar 3 affords a solid location resistant to movement or pullout.

The thicker cross-section adjacent cannulation 9 of blade 2 seen in FIG. 3 reduces flexing of blade 2 in response to loads applied in the transverse direction towards the posterior or anterior of the patients body, whereas the somewhat reduced cross-section adjacent side surfaces 6 allows the blade to be inserted with minimal stripping of tissue. Side surfaces 6 present more surface area than the sides of flat, helical blades known in the art to resist cutting through cancellous bone in directions aligned with the width of blade 2.

It will be appreciated that those skilled in the art may devise numerous modifications and embodiments. It is intended that the following claims cover all such modifications and embodiments that fall within the true spirit and scope of the present invention.

What is claimed is:
1. An implant for a bone said implant comprising:
    a body member having a lateral portion and a medial portion and a helically twisted blade extending along the body and having a longitudinal axis;
    said lateral portion having a circumferential collar extending in a plane perpendicular to said longitudinal axis; and
    said circumferential collar having an attachment element for attaching a tissue fastener for repairing tissue surrounding the bone, said circumferential collar having a central hole configured with threads to releasably engage a tool for positioning the implant in the bone.
2. The implant of claim 1 wherein the attachment element comprises a hole for securing the tissue fastener.
3. The implant of claim 2 wherein the hole is threaded.
4. The implant of claim 1 wherein the body member further comprises a central portion between the lateral and medial portions, the central portion having a cross section and a maximum thickness adjacent said longitudinal axis which gradually tapers to a minimum thickness apart from said longitudinal axis.
5. The implant of claim 1 further comprising a cannulation extending through the body member along said longitudinal axis from said medial portion to said lateral portion.
6. The implant of claim 1 wherein the medial portion further comprises a medially extending medial end portion having surfaces configured for cutting through the bone.
7. The implant of claim 1 further comprising a medial end portion extending medially from the medial portion, said medial end portion comprising:
    first and second cutting regions; and
    a transverse axis, said first and second cutting regions asymmetrically disposed about said transverse axis.
8. The implant of claim 7 wherein said first and second cutting regions further comprise cutting edges, said cutting edges forming an angle of about thirty degrees to said transverse axis.
9. The implant of claim 8 wherein said first and second cutting regions further comprise an angled cutting surface.
10. The implant of claim 9 wherein said angled cutting surfaces form an angle of from about five to sixty degrees with respect to said longitudinal axis.
11. The implant of claim 1 wherein the lateral portion of the helically twisted blade is twisted about one fourth turn with respect to the medial portion.
12. An osteosynthetic apparatus for fixing a broken humerus comprising:
    the implant of claim 1;
    a securing member comprising an elongated nail having a proximal securing portion configured to occupy an upper portion of the humeral shaft and a distal portion configured to occupy a lower portion of the humeral shaft; and
    the proximal securing portion having at least one longitudinal bore configured to accommodate the implant.
13. The apparatus of claim 12 wherein the circumferential collar includes a plurality of holes suitable for anchoring a suture.
14. A method for fixing a broken humerus having a head comprising:
    implanting the implant of claim 1 in the humerus with the medial portion of the twisted blade inside the head of the humerus.
15. The method of claim 14 further comprising anchoring soft tissue to the implant utilizing sutures secured to the attachment element.
16. An implant for a humerus said implant comprising:
    a body member having a lateral portion and a medial portion and a helically twisted blade extending along the body and having a longitudinal axis, and wherein the body member further comprises a central portion between the lateral and medial portions, the central portion having a cross section and a maximum thick- ness adjacent said longitudinal axis and which gradually tapers to a minimum thickness apart from said longitudinal axis;

said lateral portion having a circumferential collar extending in a plane perpendicular to said longitudinal axis; and said circumferential collar having an attachment element for attaching a tissue fastener for repairing tissue surrounding the humerus.

17. The implant of claim 16 wherein the attachment element comprises a hole for securing the tissue fastener.

18. The implant of claim 17 wherein the hole is threaded.

19. The implant of claim 16 wherein the lateral portion of the helically twisted blade is twisted about one fourth turn with respect to the medial portion.

20. The implant of claim 16 wherein said circumferential collar includes a central hole configured with threads to releasably engage a tool for positioning the implant in the humerus.

* * * * *